United States Patent [19]

Murtha

[11] 4,201,632

[45] May 6, 1980

[54] SEPARATION OF PHENOL-, CYCLOHEXANONE-, AND CYCLOHEXYLBENZENE-CONTAINING MIXTURES EMPLOYING A NITRILE AS EXTRACTION DISTILLATION SOLVENT

[75] Inventor: Timothy P. Murtha, Bartlesville, Okla.

[73] Assignee: Phillips Petroleum Company, Bartlesville, Okla.

[21] Appl. No.: 971,169

[22] Filed: Dec. 20, 1978

[51] Int. Cl.² ............... B01D 3/40; C07C 37/22; C07C 45/24
[52] U.S. Cl. ............................. 203/51; 203/60; 568/749; 568/366
[58] Field of Search ............ 203/51, 60; 260/586 R, 260/586 P; 568/749

[56] References Cited

U.S. PATENT DOCUMENTS

| 3,248,308 | 4/1966 | Haskell | 203/60 |
| 4,016,049 | 4/1977 | Fozzard | 568/749 |
| 4,019,965 | 4/1977 | Fozzard | 568/749 |
| 4,021,490 | 5/1977 | Hudson | 260/586 P |

Primary Examiner—Wilbur L. Bascomb, Jr.

[57] ABSTRACT

Phenol-, cyclohexanone-, and cyclohexylbenzene-containing mixtures are extractively distilled to provide an overhead of cyclohexanone substantially free of phenol and cyclohexylbenzene and a bottoms containing phenol and cyclohexylbenzene, substantially free of cyclohexanone by employing a nitrile solvent.

7 Claims, No Drawings

SEPARATION OF PHENOL-, CYCLOHEXANONE-, AND CYCLOHEXYLBENZENE-CONTAINING MIXTURES EMPLOYING A NITRILE AS EXTRACTION DISTILLATION SOLVENT

This invention relates to the separation of phenol from its azeotropes, including phenol/cyclohexanone azeotrope, which may be in the presence of cyclohexylbenzene. In one of its aspects, the invention relates to the recovery of phenol and cyclohexanone from the cleavage products resulting from cleavage of the oxidation product of cyclohexylbenzene namely cyclohexylbenzene hydroperoxide which upon cleavage produces a mixture containing phenol, cyclohexanone, and any unreacted cyclohexylbenzene.

In one of its concepts, the invention provides a process for extractive distillation of a mixture containing phenol and cyclohexanone employing as solvent or extractive distillation agent a nitrile as herein described. In another of its concepts the invention provides such a process for extractive distillation of a mixture containing phenol, cyclohexanone, and cyclohexylbenzene resulting from cleavage of the oxidation process of cyclohexylbenzene, i.e., cyclohexylbenzene hydroperoxide.

In a further concept of the invention, the extractive distillation yields an overhead product of high purity cyclohexanone of the order of about 98–99 wt % or higher.

In a still further concept of the invention, the extractive distillation bottoms product will consist essentially of phenol and the nitrile, as well as any cyclohexylbenzene which may have been present, is subjected to distillation to recover phenol and any cyclohexylbenzene as an overhead and a bottoms stream containing a nitrile solvent, which can be passed to the extracted distillation column.

It is an object of this invention to separate mixtures containing phenol and cyclohexanone which also can contain cyclohexylbenzene. It is another object of this invention to provide an extractive distillation agent or solvent to separate mixtures as herein described. It is a still further object of the invention to provide an extractive distillation operation comprising a mixture of one or more agents or solvents also described herein.

Other aspects, concepts, objects, and the several advantages of the invention are apparent from a study of this disclosure and the appended claims.

According to the present invention, a mixture containing phenol and cyclohexanone, which mixture may contain cyclohexylbenzene, is extractively distilled and thus separated to produce as an overhead product a fraction containing essentially cyclohexanone and a kettle product containing phenol, cyclohexylbenzene when present, and the agent or solvent.

Cyclohexylbenzene can be converted to phenol and cyclohexanone via cyclohexylbenzene hydroperoxide. The acid catalyzed cleavage of cyclohexylbenzene hydroperoxide in the presence of unoxidized cyclohexylbenzene results in a mixture of cyclohexylbenzene, phenol, and cyclohexanone. This mixture is difficult to separate by conventional distillation techniques because phenol and cyclohexanone form an azeotrope (boiling point 184° C. at atmospheric pressure) containing about 72 wt. % phenol. In addition, cyclohexylbenzene codistills with this azeotrope.

In the practice of the process of this invention, any mixture of phenol, cyclohexanone, and cyclohexylbenzene can be used as the feed mixture to be separated. It is within the scope of this invention to remove by suitable methods a portion of any of the components from the mixture to be separated before the extractive distillation with the nitrile solvent. For example, any excess of cyclohexanone over the quantity present in the azeotrope, can be first distilled from the mixture as an essentially pure material. Since cyclohexylbenzene codistills with the phenol/cyclohexanone azeotrope in quantities of about 2 to about 10 wt %, any excess of cyclohexylbenzene over that amount can be separated by fractional distillation in taking the phenol/cyclohexanone mixture containing about 2 to 10 wt % cyclohexylbenzene overhead.

It is also within the scope of this invention to remove essentially all of the cyclohexylbenzene from the mixture by suitable techniques, such as extraction or extractive distillation, to obtain a mixture of phenol and cyclohexanone that can be separated by the extractive distillation of this invention.

The nitrile solvent used in the extractive distillation of this invention can contain up to 30 carbon atoms and is represented by the following general formula:

$$R(CN)_m$$

wherein m is an integer from 1 to 4 and R is selected from a group consisting of hydrocarbyl and substituted hydrocarbyl radicals. The term "hydrocarbyl" means the mono- or polyvalent radical obtained by removing from one to four hydrogen atoms from the parent hydrocarbon.

Illustrative of such groups are the radicals derived from alkanes, cycloalkanes, alkenes, cycloalkenes, aromatics, alkylaromatics, and the like, and mixtures thereof. The term "substituted hydrocarbyl" means the hydrocarbyl groups described above substituted with one or more inert substituents. The term "inert substituents" means that the substituent is inert under the conditions utilized in the process of this invention, i.e., does not enter into reaction with any of the components present during the extractive distillation. Examples of inert substituents include alkoxy, such as methoxy, ethoxy, propoxy, octyloxy, and the like, and mixtures thereof and halogen such as fluoro, chloro, bromo, iodo, and mixtures thereof.

It is generally preferred that the boiling point of the nitrile should be above the boiling point of cyclohexylbenzene (238° C. at atmospheric pressure), when present in the mixture to be separated, or above the boiling point of phenol (182° C. at atmospheric pressure), when cyclohexylbenzene is not present, to facilitate the separation of the solvent for recycling by fractional distillation. However, low levels of phenol and/or cyclohexylbenzene (up to a total of about 10 wt % cyclohexylbenzene and/or phenol) can be present in the recovered and recycled solvent with no detrimental effect on the extractive distillation. For ease of handling, it is generally preferred that the nitrile be a liquid or low melting (below about 80° C.) solid.

Specific examples of nitriles that are suitable for the extractive distillation of this invention include 2-bromobenzonitrile, p-chlorophenylacetonitrile, cinnamonitrile, 1-cyanonaphthalene, adiponitrile, 2,3-dimethoxybenzonitrile, 3,4-dimethoxyphenylacetonitrile, 2,2-diphenylpropionitrile, tridecanenitrile, dodecanedinitrile, 5-methylenenonanedinitrile, 5-methyl-4-nonenedinitrile, 2,4-dimethyl-4-octenedinitrile, 2-methyl-4-methyleneoctanedinitrile, 2,4-dimethyl-3-octenedinitrile, 2,6-dimethyl-4-methyleneheptanedinitrile, 2,4,6-trimethyl-3-heptenedinitrile, 5-methylnonanedinitrile, 2,4-dimethyloctanedinitrile, 2,4,6-trimethylheptanedinitrile, and the like, and mixtures thereof.

The presently preferred solvents for the extractive distillation are:

a. The dinitrile reaction product mixture obtained by the reaction of isobutylene with acrylonitrile. This dinitrile reaction product mixture generally contains 5-methyl-4-nonenedinitrile, 2,4-dimethyl-4-octenedinitrile, 2,4-dimethyl-3-octenedinitrile, 2,4,6-trimethyl-3-heptenedinitrile, 5-methylenenonanedinitrile, 2-methyl-4-methyleneoctanedinitrile, and 2,6-dimethyl-4-methyleneheptanedinitrile. In this mixture, 5-methyl-4-nonenedinitrile and 5-methylenenonenedinitrile generally form the majority.

b. the dinitrile mixture obtained by the catalytic hydrogenation of the olefinic groups in the mixture from the mixture in (a) above. This dinitrile mixture generally contains 5-methylnonanedinitrile, 2,4-dimethyloctanedinitrile, and 2,4,6-trimethylheptanedinitrile.

The extractive distillation of this invention can be carried out under a variety of conditions. The volume ratio of the nitrile solvent to feedstream will be broadly from about 0.1/1 to about 20/1, preferably 1/1 to 5/1. To avoid possible thermal decomposition or other reactions during the extractive distillation, head temperatures below about 150° C. and preferably below 100° C. are generally used with a reduced pressure sufficient to allow the separation to occur.

In the process of this invention, a feed mixture containing phenol, cyclohexanone, and cyclohexylbenzene is passed to an extractive distillation column. The nitrile solvent of this invention is introduced into the extractive distillation column at a point above the point of introduction of the feed mixture.

An overhead stream consisting of cyclohexanone substantially free of phenol and cyclohexylbenzene is withdrawn from the extractive distillation column. A bottom stream consisting primarily of phenol, cyclohexylbenzene, and the nitrile solvent is withdrawn from the extractive distillation column and passed to a distillation column. In the distillation column, the phenol-cyclohexylbenzene-nitrile mixture is separated into an overhead stream containing phenol and cyclohexylbenzene and a bottom stream containing the nitrile solvent which is passed to the extractive distillation column. Makeup nitrile solvent can be added if necessary. The phenol-cyclohexylbenzene overhead stream can be passed to another separation stage to separate this mixture.

When the mixture to be separated consists of phenol and cyclohexanone, e.g., when cyclohexylbenzene has been first removed from a phenol-cyclohexanone-cyclohexylbenzene mixture, the bottom stream from the extractive distillation column will contain phenol and the nitrile solvent and the overhead stream from the distillation column will contain phenol.

EXAMPLES

In the following examples, extractive distillations were conducted in an electrically heated 0.75" (19 mm) diameter×36" (914 mm) length column containing 0.25" (6.4 mm) Por-Pak stainless steel perforated screen packing. The solvent was fed through a rotameter and heating section to an introduction port 3" (76 mm) from the top of the column. The mixture to be separated was fed through a rotameter and heating section of an introduction port 18" (457 mm) from the top of the column. The overhead and kettle products were collected and then analyzed by gas-liquid phase chromatography (glpc) on a Hewlett Packard 5710A chromatograph equipped with a flame ionization detector.

Fractional distillations were conducted with an electrically heated 0.75" (19 mm) diameter×8" (203 mm) length column containing 0.25" (6.4 mm) stainless steel Heli-Pak packing. The overhead fractions and the kettle product were collected and then analyzed by glpc.

The mixtures to be separated were prepared from commerical, reagent grade phenol and cyclohexanone and cyclohexylbenzene prepared by the reductive alkylation of benzene.

The extractive distillation solvent utilized in the examples is a mixture of olefinically unsaturated dinitriles prepared by the reaction of isobutylene with acrylonitrile. This reaction mixture consists of approximately 52 wt % 5-methylenenonanedinitrile, approximately 35 wt % 5-methyl-4-nonenedinitrile, approximately 12 wt % of the combination of 2,4-dimethyl-4-octenedinitrile, 2-methyl-4-methyleneoctanedinitrile, and 2,4-dimethyl-3-octenedinitrile, and approximately 1 wt % of the combination of 2,6-dimethyl-4-methyleneheptanedinitrile, and 2,4,6-trimethyl-3-heptenedinitrile. For simplicity, the above described reaction mixture will be called diadduct.

EXAMPLE I

A run was conducted according to the instant invention utilizing diadduct as the solvent for the extractive distillation of a mixture containing 68 wt % phenol, 27 wt % cyclohexanone, and 5 wt % cyclohexylbenzene. This mixture was fed to the extractive distillation column at a rate of about 24 ml/hour. The extractive distillation conditions were 50 mm Hg, 54°–58° C. head temperature, and a 4/1 solvent/feed volume ratio. Over a 6 hour run time, the overhead fractions contained cyclohexanone and only about 0.1 wt % cyclohexylbenzene. Any phenol present was below the detection limit of the analytical process. The cyclohexanone collected was about 89 wt % of the amount of cyclohexanone fed to the column during the run.

The results of this run demonstrate the process of this invention utilizing diadduct as the solvent for the separation of cyclohexanone from a mixture of cyclohexanone, phenol, and cyclohexylbenzene.

EXAMPLE II

Another run was conducted according to this invention utilizing diadduct as the solvent for the extractive distillation of a mixture containing 68 wt % phenol, 27 wt % cyclohexanone, and 5 wt % cyclohexylbenzene. This run was conducted in a manner similar to the run in Example I except the solvent/feed volume ratio was reduced to 2.3/1. Over a 4 hour run time, the overhead fractions contained cyclohexanone, about 0.02 wt % phenol, and about 0.33 wt % cyclohexylbenzene. The cyclohexanone collected was about 79 wt % of the amount of cyclohexanone fed to the column during the run.

The results of this run demonstrate operability of this invention utilizing diadduct as the solvent for the separation of cyclohexanone from a mixture of cyclohexanone, phenol, and cyclohexylbenzene.

EXAMPLE III

Another run was conducted according to this invention utilizing diadduct as the extractive distillation solvent for the extractive distillation of a mixture containing 68 wt % phenol, 27 wt % cyclohexanone, and 5 wt % cyclohexylbenzene. This run was conducted in a manner similar to the run in Example I except the pressure was increased to 120 mm Hg, the head temperature was about 78°-83° C., and the solvent/feed volume ratio was reduced to 2.3/1. Over a 4 hour run time, the overhead fractions contained cyclohexanone, about 1.3 wt % phenol, and about 5.9 wt % cyclohexylbenzene. The cyclohexanone collected was about 80 wt % of the amount of cyclohexanone fed to the column during the run.

The kettle products from this run and the run in Example II were combined and fractionally distilled at 50 mm Hg to separate overhead fractions containing predominantly phenol and cyclohexylbenzene from a kettle product which was essentially pure diadduct.

The results of this run indicate that a less satisfactory separation of cyclohexanone from the other mixture components than were observed in Examples I and II (at 50 mm Hg) occurs at distillation pressures above the pressures used in Examples I and II, e.g., at 120 mm Hg. In addition, the recovery of the solvent by fractional distillation for recycle to the extractive distillation column was demonstrated.

Reasonable variation and modification are possible within the scope of the foregoing disclosure and the appended claims to the invention, the essence of which is that there has been found that extractive distillation of a mixture of phenol and cyclohexanone, and cyclohexylbenzene when it is present, can be accomplished with good yields of high purity cyclohexanone as overhead employing a nitrile as herein described.

I claim:

1. An extractive distillation of a mixture containing phenol and cyclohexanone, which mixture may also contain cyclohexylbenzene, which comprises distilling said mixture in the presence of a solvent comprising at least one nitrile which contains up to about 30 carbon atoms and which can be represented by the following general formula:

$$R(CN)_m$$

wherein m is an integer from 1 to 4 and wherein R is selected from a group consisting of hydrocarbyl and substituted hydrocarbyl radicals.

2. An extractive distillation according to claim 1 wherein the solvent is at least one nitrile selected from the following: 2-bromobenzonitrile, p-chlorophenylacetonitrile, cinnamonitrile, 1-cyanonaphthalene, adiponitrile, 2,3-dimethoxybenzonitrile, 3,4-dimethoxyphenylacetonitrile, 2,2-diphenylpropionitrile, tridecanenitrile, dodecanedinitrile, 5-methylenenonanedinitrile, 5-methyl-4-nonenedinitrile, 2,4-dimethyl-4-octenedinitrile, 2-methyl-4-methyleneoctanedinitrile, 2,4-dimethyl-3-octenedinitrile, 2,6-dimethyl-4-methyleneheptanedinitrile, 2,4,6-trimethyl-3-heptenedinitrile, 5-methylnonanedinitrile, 2,4-dimethyloctanedinitrile, 2,4,6-trimethylheptanedinitrile, and the like.

3. An extractive distillation according to claim 1 wherein the solvent is a dinitrile reaction product mixture obtained by the reaction of isobutylene with acrylonitrile.

4. An extractive distillation according to claim 1 wherein the solvent contains the following: 5-methyl-4-nonenedinitrile, 2,4-dimethyl-4-octenedinitrile, 2,4-dimethyl-3-octenedinitrile, 2,4,6-trimethyl-3-heptenedinitrile, 5-methylenenonanedinitrile, 2-methyl-4-methyleneoctanedinitrile, and 2,6-dimethyl-4-methyleneheptanedinitrile.

5. An extractive distillation according to claim 4 wherein the major proportion of the solvent consists of 5-methyl-4-nonenedinitrile and 5-methylenenonenedinitrile.

6. An extractive distillation according to claim 1 wherein the solvent is a dinitrile mixture obtained by the catalytic hydrogenation of the olefinic groups of the following: 5-methyl-4-nonenedinitrile, 2,4-dimethyl-4-octenedinitrile, 2,4-dimethyl-3-octenedinitrile, 2,4,6-trimethyl-3-heptenedinitrile, 5-methylenenonanedinitrile, 2-methyl-4-methyleneoctanedinitrile, and 2,6-dimethyl-4-methyleneheptanedinitrile.

7. An extractive distillation according to claim 6 wherein the solvent contains 5-methylnonanedinitrile, 2,4-dimethyloctanedinitrile, and 2,4,6-trimethylheptanedinitrile.

* * * * *